(12) United States Patent
Hwang et al.

(10) Patent No.: US 8,415,277 B2
(45) Date of Patent: Apr. 9, 2013

(54) BI-FUNCTIONAL COMPOUND POSITIVELY CHARGED AT FIRST PH AND NEGATIVELY CHARGED AT SECOND PH, SOLID SUPPORT COMPRISING THE BI-FUNCTIONAL COMPOUND, AND METHOD OF ISOLATING NUCLEIC ACID USING THE SAME

(75) Inventors: Kyu-youn Hwang, Yongin-si (KR); Joon-ho Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 466 days.

(21) Appl. No.: 12/555,676

(22) Filed: Sep. 8, 2009

(65) Prior Publication Data

US 2010/0063267 A1  Mar. 11, 2010

(30) Foreign Application Priority Data

Sep. 9, 2008 (KR) .................. 10-2008-0088955

(51) Int. Cl.
*C40B 80/00* (2006.01)
*C07C 409/44* (2006.01)
*C12Q 1/68* (2006.01)
*A61K 51/00* (2006.01)

(52) U.S. Cl.
USPC .............. 506/42; 435/6.1; 435/135; 435/136; 562/6; 424/1.53

(58) Field of Classification Search ............... 424/1.53; 562/6; 435/6, 135, 136; 506/42
See application file for complete search history.

(56) References Cited

U.S. PATENT DOCUMENTS

| | | | |
|---|---|---|---|
| 5,085,779 A | 2/1992 | Crane et al. | |
| 5,186,677 A | 2/1993 | Christensen et al. | |
| 5,945,520 A | 8/1999 | Burton et al. | |
| 6,043,474 A | 3/2000 | Gates et al. | |
| 6,183,973 B1 | 2/2001 | Wright et al. | |
| 6,310,199 B1 | 10/2001 | Smith et al. | |
| 6,605,454 B2 | 8/2003 | Barenburg et al. | |
| 6,914,137 B2 | 7/2005 | Baker | |
| 7,439,023 B2 * | 10/2008 | Hwang et al. ............ | 435/6.16 |
| 2001/0001851 A1 | 5/2001 | Piety et al. | |
| 2001/0018513 A1 | 8/2001 | Baker | |
| 2002/0115201 A1 | 8/2002 | Barenburg et al. | |
| 2003/0180936 A1 | 9/2003 | Memarzadeh et al. | |
| 2005/0142255 A1 | 6/2005 | Blankenbeckler et al. | |
| 2006/0134675 A1 | 6/2006 | Yoo et al. | |
| 2006/0141556 A1 | 6/2006 | Jeong et al. | |
| 2006/0154284 A1 | 7/2006 | Hwang et al. | |
| 2006/0228737 A1 | 10/2006 | Hwang et al. | |
| 2006/0264621 A1 | 11/2006 | Hwang et al. | |
| 2009/0005265 A1 | 1/2009 | Hwang et al. | |
| 2009/0012302 A1 | 1/2009 | Hwang et al. | |

FOREIGN PATENT DOCUMENTS

| | | | |
|---|---|---|---|
| EP | 0707077 | A2 | 4/1996 |
| EP | 1674570 | A2 | 6/2006 |
| EP | 1715039 | * | 10/2006 |
| EP | 1724016 | A1 | 11/2006 |
| KR | 1020060108125 | A | 10/2006 |
| WO | 9929703 | A2 | 6/1999 |
| WO | 0069872 | A2 | 11/2000 |
| WO | 2004055213 | A1 | 7/2004 |
| WO | 2005093065 | A1 | 10/2005 |

OTHER PUBLICATIONS

Reddy (Journal of Applied Polymer Science vol. 75, pp. 1721-1727, 2000).*
Korean Office Action mailed Jul. 19, 2010 for KR Application No. 1020080088955; with English Translation.
European Search Report for corresponding European Patent Application No. 09 16 9837, dated Nov. 21, 2012, 10 pages.
McLaughlin, Larry W., "Mixed-Mode Chromatography of Nucleic Acids," Chemical Reviews, American Chemical Society, vol. 89, No. 2, Jan. 1, 1989, pp. 309-319.
Pompe, Tilo, et al., "Maleic Anhydride Copolymers—A Versatile Platform for Molecular Biosurface Engineering," Biomacromolecules, American Chemical Society, vol. 4, No. 4, Jan. 1, 2003, pp. 1072-1079.
Spargo, B. J., et al., "Spatially controlled adhesion, spreading, and differentiation of endothelial cells on self-assembled molecular monolayers," Cell Biology, Proceedings of the National Academy of Sciences. USA, vol. 91, Nov. 1, 1994, pp. 11070-11074.

* cited by examiner

*Primary Examiner* — Jezia Riley
(74) *Attorney, Agent, or Firm* — Cantor Colburn LLP

(57) ABSTRACT

Provided are a bi-functional compound that is positively charged at a first pH and negatively charged at a second pH, a solid support having the bi-functional compound immobilized thereon, and a method of isolating a nucleic acid, including: binding the bi-functional compound with a nucleic acid at a first pH and isolating the nucleic acid from the bi-functional compound at a second pH.

15 Claims, No Drawings

BI-FUNCTIONAL COMPOUND POSITIVELY CHARGED AT FIRST PH AND NEGATIVELY CHARGED AT SECOND PH, SOLID SUPPORT COMPRISING THE BI-FUNCTIONAL COMPOUND, AND METHOD OF ISOLATING NUCLEIC ACID USING THE SAME

CROSS-REFERENCE TO RELATED APPLICATIONS

This application claims priority to Korean Patent Application No. 10-2008-0088955, filed on Sep. 9, 2008, and all the benefits accruing therefrom under 35 U.S.C. 119, the content of which in its entirety is herein incorporated by reference.

BACKGROUND

1. Field

One or more embodiments relate to a bi-functional compound, positively charged at a first pH and negatively charged at a second pH, a solid support comprising the bi-functional compound, and a method of isolating a nucleic acid using the same.

2. Description of the Related Art

Methods of isolating a nucleic acid by using a pH-dependent ion exchange material typically include, for example isolating a nucleic acid by treating a solution of the nucleic acid with a material having an ionizable group, such as an acidic functional group or basic functional group, which is positively charged at a first pH, thereby binding the nucleic acid, and subsequently releasing the nucleic acid at a second pH that is higher than the first pH. Examples of materials having such an ionizable group include N-2-acetamido-2-aminoethanesulfonic acid ("ACES"), N-2-acetamido-2-imidodiacetic acid ("ADA"), N-trihydroxymethyl-methyl-2-aminoethanesulfonic acid ("TES") and tris(hydroxymethyl)aminoethane ("Tris"), each of which is a common, commercially available buffer compound. In other methods of isolating a nucleic acid, a pH dependent ion exchange material may be used which includes a support such as a silica-coated magnetic particle with a plurality of first ion exchange ligands, in which each first ion exchange ligand includes an aromatic hydrocarbon ring, a spacer which covalently attaches the ion exchange ligand to the aromatic hydrocarbon ring, and a linker which includes an alkylene chain and which is attached to the silica magnetic particle at one end and to the spacer at the opposite end.

However, despite these methods, there is remains a need for materials which bind efficiently to a nucleic acid, and which also efficiently release the nucleic acid in the reaction of isolating the nucleic acid.

SUMMARY

One or more embodiments include a compound that is positively charged at a first pH and negatively charged at a second pH and a substrate on which the bi-functional compound is immobilized.

In an embodiment, the bi-functional compound positively charged at a first pH and negatively charged at a second pH, is represented by Formula I below:

$$Q-X-Q_1 \qquad \text{(Formula I)}$$

wherein Q or $Q_1$ is a group represented by $-X_1-R_1-Y_1$ where $X_1$ is $-O-$, $-S-$, or $-NR_2-$ or a combination comprising at least one of the foregoing, where $R_2$ is hydrogen, halogen, and a substituted or unsubstituted $C_1-C_{10}$ alkyl, $R_1$ is a substituted or unsubstituted $C_1-C_{10}$ alkylene, a substituted or unsubstituted $C_3-C_{10}$ cycloalkylene, a substituted or unsubstituted $C_2-C_{10}$ alkenylene, a substituted or unsubstituted $C_2-C_{10}$ alkynylene, or a combination comprising at least one of the foregoing, $Y_1$ is a group represented by

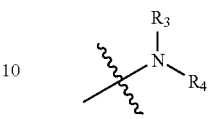

where $R_3$ and $R_4$ are each independently hydrogen, a substituted or unsubstituted $C_1-C_{10}$ alkyl, a substituted or unsubstituted $C_3-C_{10}$ cycloalkyl, a substituted or unsubstituted $C_2-C_{10}$ alkenyl, a substituted or unsubstituted $C_2-C_{10}$ alkynyl, or a combination comprising at least one of the foregoing, or $R_3$ and $R_4$ are bound to each other to form an alicyclic or aromatic group, or $Y_1$ is a group that is represented by

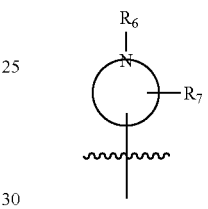

and has a 4- to 8-membered alicyclic ring or a 6- to 8-membered aromatic ring where $R_6$ and $R_7$ are each independently hydrogen, halogen, a substituted or unsubstituted $C_1-C_{10}$ alkyl, a substituted or unsubstituted $C_3-C_{10}$ cycloalkyl, a substituted or unsubstituted $C_2-C_{10}$ alkenyl, a substituted or unsubstituted $C_2-C_{10}$ alkynyl, or a combination comprising at least one of the foregoing, with a proviso that $R_6$ is not halogen, at least one of Q and $Q_1$ has a primary or secondary amino group, X is a compound represented by

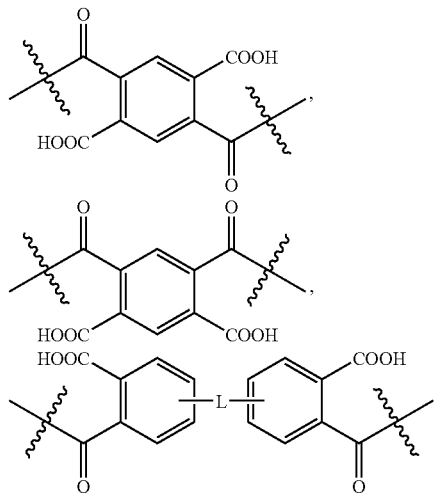

wherein L is a bond, $-O-$, $-CO-$, $-S-$, $-SO_2-$, $-CH_2-$, $-C(CH_3)_2-$, $-C(CF_3)_2-$, or a combination comprising at least one of the foregoing,

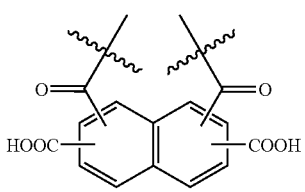

wherein the carbonyl group and the carboxyl group are substituted at any available carbon position except for a ring connection portion,

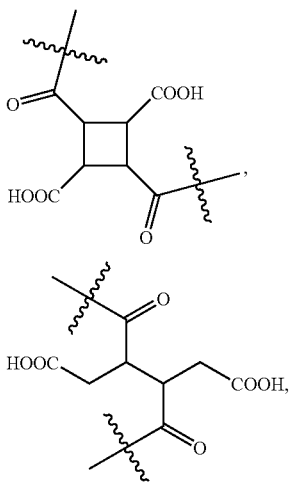

or a combination comprising at least one of the foregoing, or a bi-functional compound that is positively charged at a first pH and negatively charged at a second pH, wherein the bi-functional compound is linked to at least one monomer comprising monomers represented by M0, M1, M2, M3, or a combination comprising at least one of the foregoing, below, and wherein the bi-functional compound comprises at least one of a monomer with A and at least one of a monomer with B,

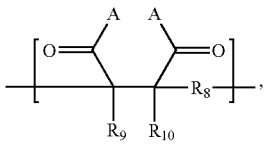

(Formula M0)

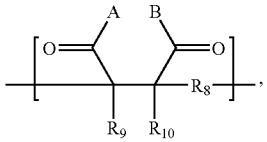

(Formula M1)

(Formula M2)

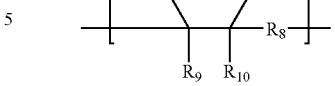

(Formula M3)

wherein A is a group represented by —OH or —$X_2$—$R_{11}$—$Y_2$ where $X_2$ is O—, —S—, —$NR_{12}$—, or a combination comprising at least one of the foregoing, where $R_{12}$ is hydrogen, halogen, a substituted or unsubstituted $C_1$-$C_{10}$ alkyl, or a combination comprising at least one of the foregoing, $R_{11}$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing, and $Y_2$ is —COOH, —$SO_3H$, —$SO_2H$, —SOH, —$H_2PO_4$, —$HPO_4^-$, —$PO_4^{2-}$, or a combination comprising at least one of the foregoing, B is a group represented by —$X_3$—$R_{13}$—$Y_3$ where $X_3$ is O—, —S—, —$NR_{14}$—, or a combination comprising at least one of the foregoing, where $R_{14}$ is hydrogen, halogen, and a substituted or unsubstituted $C_1$-$C_{10}$ alkyl, $R_{13}$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, and a substituted or unsubstituted $C_2$-$C_{10}$ alkynylene, or a combination comprising at least one of the foregoing, $Y_3$ is a group represented by

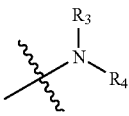

where $R_3$ and $R_4$ are each independently hydrogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing, or $R_3$ and $R_4$ are bound to each other to form an alicyclic or aromatic ring, or $Y_3$ is a group that is represented by

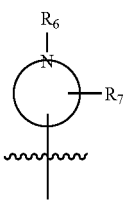

and has a 4- to 8-membered alicyclic ring or a 6- to 8-membered aromatic ring where $R_6$ and $R_7$ are each independently hydrogen, halogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing, with a proviso that $R_6$ is not halogen, $R_8$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing, $R_9$ and $R_{10}$ are each independently hydrogen, halogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing, wherein the bi-functional compound comprising A and B has a polymerization degree of about 2 to about 30,000.

In another embodiment, a solid support on which a bi-functional compound is immobilized, includes a substrate, and the bi-functional compound immobilized on the substrate.

In another embodiment, a method of isolating a nucleic acid includes contacting a bi-functional compound with a sample comprising a nucleic acid at a first pH and exposing the bi-functional compound with the nucleic acid bound thereto at a second pH that is higher than the first pH to release the nucleic acid from the bi-functional compound.

In another embodiment, a solid support on which a bi-functional compound is immobilized, derives from the sequential reaction product of a substrate, a surface treatment agent, a dianhydride or polyanhydride, and a nitrogen-containing compound, wherein the bi-functional compound is positively charged at a first pH and negatively charged at a second pH.

DETAILED DESCRIPTION OF THE EMBODIMENTS

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

In this regard, the present embodiments may have different forms and should not be construed as being limited to the descriptions set forth herein. Accordingly, the embodiments are merely described below, by referring to the figures, to explain aspects of the present description.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, regions, integers, steps, operations, elements, and/or components, but do not preclude the presence or addition of one or more other features, regions, integers, steps, operations, elements, components, and/or groups thereof. All ranges and endpoints reciting the same feature are independently combinable.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the chemical structures herein, and unless otherwise indicated, all bonds which terminate without specifying a terminal group are broken bonds and represent points of attachment to an unspecified group. For example, the group

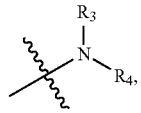

which specifies groups $R_3$ and $R_4$ attached to a nitrogen atom, has a point of attachment through the broken bond to another substructure.

Also in the chemical structures herein, where "halogen" is specified, it will be understood to mean fluorine, chlorine, bromine, iodine, or a combination comprising at least one of the foregoing. In an exemplary embodiment, where halogen is specified, the halogen may be fluorine, chlorine, or a combination of these.

One or more embodiments provide a bi-functional compound that is positively charged at a first pH and negatively charged at a second pH, the compound represented by Formula I below:

$$Q\text{-}X\text{-}Q_1 \quad \text{(Formula I)}$$

wherein Q or $Q_1$ is a group represented by —$X_1$—$R_1$—$Y_1$ where $X_1$ is —O—, —S—, or —$NR_2$— or a combination comprising at least one of the foregoing, where $R_2$ is hydrogen, halogen, a substituted or unsubstituted $C_1$-$C_{10}$ alkyl, or a combination comprising at least one of the foregoing, $R_1$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing, $Y_1$ is a group represented by

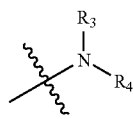

where $R_3$ and $R_4$ are each independently hydrogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing, or $R_3$ and $R_4$ are bound to each other to form an alicyclic or aromatic group, or $Y_1$ is a group that is represented by

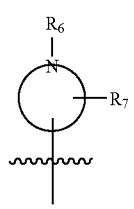

and has a 4- to 8-membered alicyclic ring or a 6- to 8-membered aromatic ring where $R_6$ and $R_7$ are each independently hydrogen, halogen with a proviso that $R_6$ is not halogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing, at least one of Q and $Q_1$ includes a primary or secondary amino group, X is a group represented by

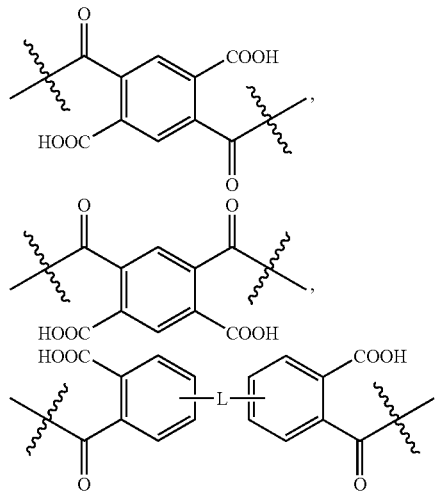

wherein L is a bond, —O—, —CO—, —S—, —SO$_2$—, —CH$_2$—, —C(CH$_3$)$_2$—, —C(CF$_3$)$_2$—, or a combination comprising at least one of the foregoing,

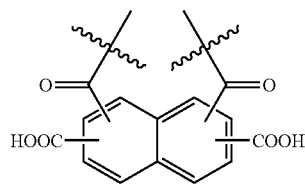

wherein the carbonyl group and the carboxyl group may be substituted at any available carbon position except for a ring connection portion,

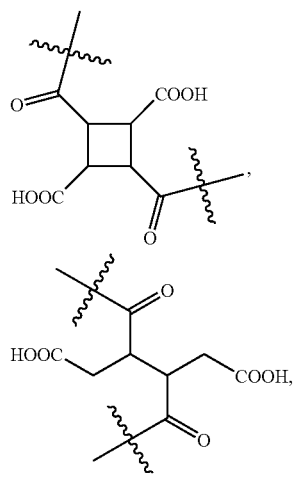

or a combination comprising at least one of the foregoing, or a bi-functional compound that is positively charged at a first pH and negatively charged at a second pH, wherein the compound is linked to at least one comprising monomers represented by M0, M1, M2, M3, or a combination comprising at least one of the foregoing, below, and wherein the bi-functional compound comprises at least one of a monomer with A and at least one of a monomer with B,

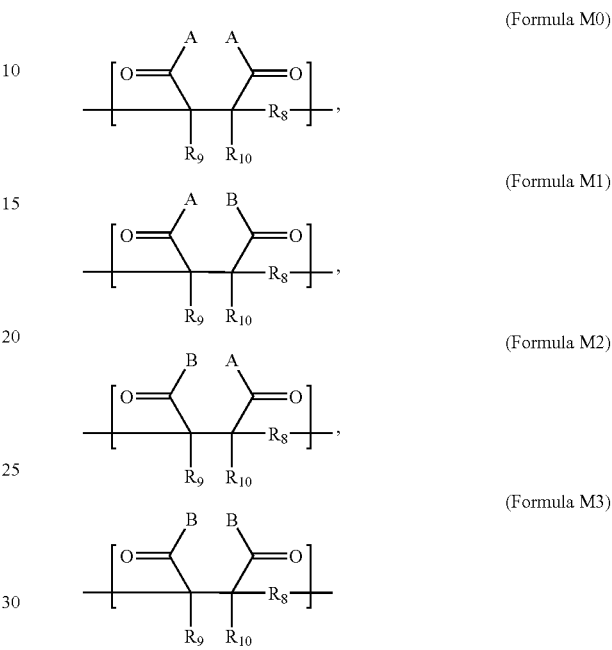

wherein A is a group represented by —OH or —X$_2$—R$_{11}$—Y$_2$ where X$_2$ is —O—, —S—, —NR$_{12}$— or a combination comprising at least one of the foregoing, where R$_{12}$ is hydrogen, halogen, a substituted or unsubstituted C$_1$-C$_{10}$ alkyl or a combination comprising at least one of the foregoing, R$_{11}$ is a substituted or unsubstituted C$_1$-C$_{10}$ alkylene, a substituted or unsubstituted C$_3$-C$_{10}$ cycloalkylene, a substituted or unsubstituted C$_2$-C$_{10}$ alkenylene, a substituted or unsubstituted C$_2$-C$_{10}$ alkynylene, or a combination comprising at least one of the foregoing, and Y$_2$ is —COOH, —SO$_3$H, —SO$_2$H, —SOH, —H$_2$PO$_4$, —HPO$_4^-$, —PO$_4^{2-}$, or a combination comprising at least one of the foregoing, B is a group represented by —X$_3$—R$_{13}$—Y$_3$ where X$_3$ is —O—, —S—, —NR$_{14}$—. or a combination comprising at least one of the foregoing, where R$_{14}$ is hydrogen, halogen, and a substituted or unsubstituted C$_1$-C$_{10}$ alkyl, R$_{13}$ is a substituted or unsubstituted C$_1$-C$_{10}$ alkylene, a substituted or unsubstituted C$_3$-C$_{10}$ cycloalkylene, a substituted or unsubstituted C$_2$-C$_{10}$ alkenylene, a substituted or unsubstituted C$_2$-C$_{10}$ alkynylene, or a combination comprising at least one of the foregoing, Y$_3$ is a group represented by

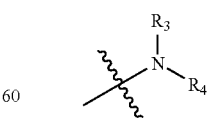

where R$_3$ and R$_4$ are each independently hydrogen, a substituted or unsubstituted C$_1$-C$_{10}$ alkyl, a substituted or unsubstituted C$_3$-C$_{10}$ cycloalkyl, a substituted or unsubstituted C$_2$-C$_{10}$ alkenyl, a substituted or unsubstituted C$_2$-C$_{10}$ alkynyl or a combination comprising at least one of the foregoing, or $R_3$ and $R_4$ are bound to each other to form an alicyclic or aromatic ring, or $Y_3$ is a group that is represented by

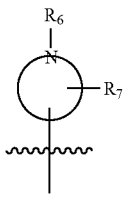

and has a 4- to 8-membered alicyclic ring or a 6- to 8-membered aromatic ring where $R_6$ and $R_7$ are each independently hydrogen, halogen with a proviso that $R_6$ is not halogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing, $R_8$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing, $R_9$ and $R_{10}$ are each independently hydrogen, halogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing. Unless otherwise specified, the term "substituted" as used herein means additional substituent groups including halogen, nitrile, hydroxy, carbonyl, carboxylic acid, carboxylate, $C_{1-20}$ alkyl, $C_{2-20}$ alkenyl, $C_{3-20}$ cycloalkyl, $C_{6-20}$ aryl, $C_{3-20}$ heteroalkyl, $C_{6-20}$ heteroaryl or a combination comprising at least one of the foregoing. The bi-functional compound comprising A and B has a degree of polymerization of about 2 to about 30,000, specifically about 2 to about 20,000, and more specifically about 2 to about 10,000.

In an embodiment, the bi-functional compound including monomers represented by M0, M1, M2, M3, or a combination thereof may include copolymers including random copolymers, block copolymers, branched copolymers, dendrimers, terpolymers, or the like, or a combination comprising at least one of the foregoing.

In Formula I, Q or $Q_1$ is a group represented by —$X_1$—$R_1$—$Y_1$ where $X_1$ is —O—, —S—, —$NR_2$—, or a combination comprising at least one of the foregoing, where $R_2$ is hydrogen, halogen, and a substituted or unsubstituted $C_1$-$C_{10}$ alkyl or a combination comprising at least one of the foregoing. Examples of the $C_1$-$C_{10}$ alkyl group include methyl, ethyl, n-propyl, isopropyl, n-butyl, isobutyl, t-butyl, or the like, or a combination comprising at least one of the foregoing. Where $R_2$ is substituted, the substituent may be halogen. Examples of —$NR_2$— can include —NH—, —N(CH$_3$)—, —N(CH$_2$CH$_3$)—, or the like, or a combination comprising at least one of the foregoing. At least one of Q and $Q_1$ includes at least one of primary and secondary amino groups.

$R_1$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing. An exemplary substituent may be halogen, —COOH, —SO$_3$H, —SO$_2$H, —SOH, —H$_2$PO$_4$, —HPO$_4^-$, —PO$_4^{2-}$, or the like, or a combination comprising at least one of the foregoing. Examples of the substituted or unsubstituted $C_1$-$C_{10}$ alkylene may be methylene, ethylene, 1,2-propylene, 1,3-propylene, 1,4-butylene, or the like, or a combination comprising at least one of the foregoing. An exemplary substituted or unsubstituted $C_3$-$C_{10}$ cycloalkylene may be 1,1- or 1,2-cyclopropylene, 1,1-, 1,2-, or 1,3-cyclobutylene, 1,1-, 1,2-, or 1,3-cyclopentylene, or the like, or a combination comprising at least one of the foregoing. An exemplary substituted or unsubstituted $C_2$-$C_{10}$ alkenylene may be ethenylene, 1,2- or 1,3-propenylene, or 1,4-but-2-enylene, or the like, or a combination comprising at least one of the foregoing. In addition, an exemplary substituted or unsubstituted $C_2$-$C_{10}$ alkynylene may be ethynylene, 1,3-propynylene, or 1,4-but-(1- or 2-)-ynylene, or the like, or a combination comprising at least one of the foregoing.

$Y_1$ is a group represented by

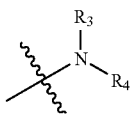

where $R_3$ and $R_4$ are each independently hydrogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or the like, or a combination comprising at least one of the foregoing, or $R_3$ and $R_4$ may be bound to each other to form an alicyclic or aromatic ring. Exemplary substituent groups include halogen, a primary, secondary or tertiary amino group, or the like, or a combination comprising at least one of the foregoing. An exemplary alicyclic ring may include a 3- to 8-membered cycloalkyl ring or cycloalkene ring, or a combination comprising at least one of the foregoing. The aromatic ring may be a 4- to 8-membered aromatic ring. $Y_1$ may be —NH$_2$, —NH(CH$_3$), or —NH(CH$_2$CH$_3$).

In addition, $Y_1$ is a group that is represented by

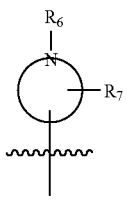

and has a 3- to 8-membered alicyclic ring or a 6- to 8-membered aromatic ring where $R_6$ and $R_7$ are each independently hydrogen, halogen with a proviso that $R_6$ is not halogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or the like, or a combination comprising at least one of the foregoing. An exemplary substituent may be halogen. $Y_1$ may be

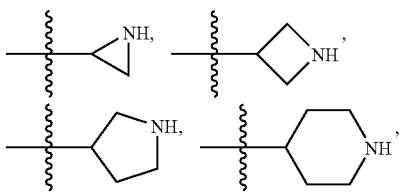

-continued

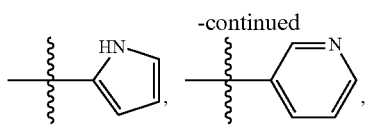

or the like, or a combination comprising at least one of the foregoing.

In Formula I, Q or $Q_1$ may be a group represented by $-X_1-R_1-Y_1$ where $R_1$ is a $C_1$-$C_{10}$ alkylene, a $C_3$-$C_{10}$ cycloalkylene, a $C_2$-$C_{10}$ alkenylene, a $C_2$-$C_{10}$ alkynylene, or the like, or a combination comprising at least one of the foregoing, each group is substituted with at least one group of $-COOH$, $-SO_3H$, $-SO_2H$, $-SOH$, $-H_2PO_4$, $-HPO_4^-$, $-PO_4^{2-}$, or a combination comprising at least one of the foregoing, and $X_1$ and $Y_1$ are each as defined above.

In Formula I, Q or $Q_1$ may be a derivative of t

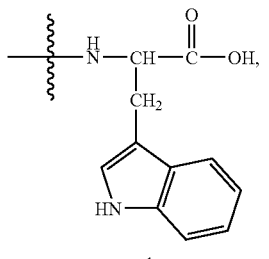
tryptophan

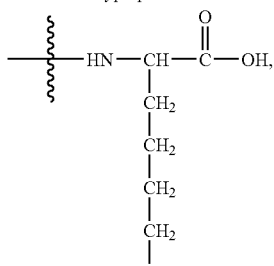
lysine

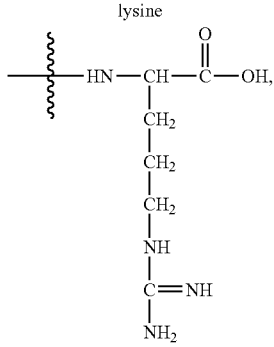
arginine

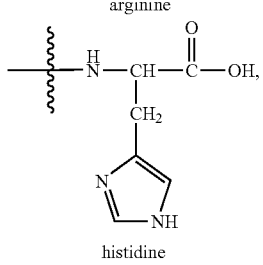
histidine or a combination comprising at least one of the foregoing.

The compound comprising A and B is a bi-functional compound that is linked to at least one monomer represented by Formulae M0, M1, M2, M3 or a combination comprising at least one of the foregoing monomers, below, wherein the monomer comprises at least one monomer with an A substituent, and at least one monomer with a B substituent.

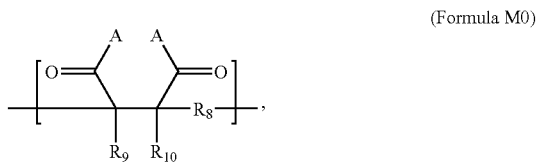
(Formula M0)

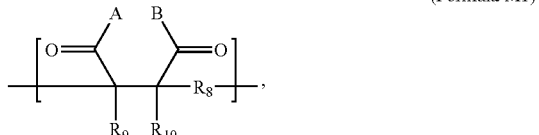
(Formula M1)

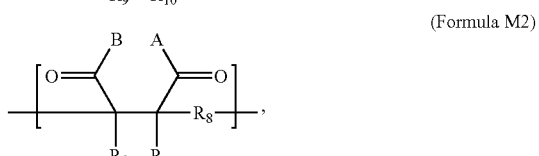
(Formula M2)

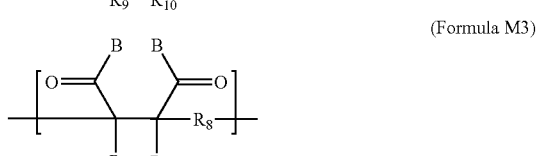
(Formula M3)

In the above formulae, A is a group represented by $-OH$ or $-X_2-R_{11}-Y_2$ where $X_2$ is $-O-$, $-S-$, $-NR_{12}-$, or a combination comprising at least one of the foregoing, where $R_{12}$ is hydrogen, halogen, a substituted or unsubstituted $C_1$-$C_{10}$ alkyl or a combination comprising at least one of the foregoing. Examples of $C_1$-$C_{10}$ alkyl include methyl, ethyl, n-propyl, isopropyl, n-butyl, isobutyl, t-butyl, or the like, or a combination comprising at least one of the foregoing. Where $R_{12}$ is substituted, the substituent may be halogen. Examples of $-NR_{12}-$ include $-NH-$, $-N(CH_3)-$, $-N(CH_2CH_3)-$ or the like, or a combination comprising at least one of the foregoing.

$R_{11}$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing. The substituent may be halogen, $-COOH$, $-SO_3H$, $-SO_2H$, $-SOH$, $-H_2PO_4$, $-HPO_4^-$, $-PO_4^{2-}$, or a combination comprising at least one of the foregoing. Exemplary substituted or unsubstituted $C_1$-$C_{10}$ alkylenes may be methylene, ethylene, 1,2-propylene, 1,3-propylene, 1,4-butylene, or the like, or a combination comprising at least one of the foregoing. Exemplary substituted or unsubstituted $C_3$-$C_{10}$ cycloalkylenes may be 1,1- or 1,2-cyclopropylene, 1,1-, 1,2-, or 1,3-cyclobutylene, 1,1-, 1,2-, or 1,3-cyclopentylene, or the like, or a combination comprising at least one of the foregoing. Exemplary substituted or unsubstituted $C_2$-$C_{10}$ alkenylenes may be ethenylene, 1,3-propenylene, 1,4-but-2-enylene, or the like, or a combination comprising at least one of the foregoing. In addition, exemplary substituted or unsubstituted $C_2$-$C_{10}$ alkynylenes may be ethynylene, 1,3-propynylene, or 1,4-but(-1- or -2-)ynylene.

Examples of $Y_2$ include $-COOH$, $-SO_3H$, $-SO_2H$, $-SOH$, $-H_2PO_4$, $-HPO_4^-$, and $-PO_4^{2-}$.

B is a group represented by —$X_3$—$R_{13}$—$Y_3$ where $X_3$ is —O—, —S—, —$NR_{14}$—, or a combination comprising at least one of the foregoing, where $R_{14}$ is hydrogen, halogen, a substituted or unsubstituted $C_1$-$C_{10}$ alkyl, or a combination comprising at least one of the foregoing. Examples of $C_1$-$C_{10}$ alkyl include methyl, ethyl, n-propyl, isopropyl, n-butyl, isobutyl, t-butyl, or the like, or a combination comprising at least one of the foregoing. Where $R_{14}$ is substituted, the substituent may be halogen. Examples of —$NR_{14}$— include —NH—, —N(CH$_3$)—, —N(CH$_2$CH$_3$)—, or the like, or a combination comprising at least one of the foregoing.

$R_{13}$ is a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, and a substituted or unsubstituted $C_2$-$C_{10}$ alkynyl. Where $R_{13}$ is substituted, examples of the substituent include halogen, —COOH, —SO$_3$H, —SO$_2$H, —SOH, —H$_2$PO$_4$, —HPO$_4^-$, —PO$_4^{2-}$, or a combination comprising at least one of the foregoing. The substituted or unsubstituted $C_1$-$C_{10}$ alkylene may be methylene, ethylene, 1,2-propylene, 1,3-propylene, 1,4-butylene or the like, or a combination comprising at least one of the foregoing. An exemplary substituted or unsubstituted $C_3$-$C_{10}$ cycloalkylene may be 1,1- or 1,2-cyclopropylene, 1,1-, 1,2-, or 1,3-cyclobutylene, or 1,1-, 1,2-, or 1,3-cyclopentylene, or the like, or a combination comprising at least one of the foregoing. An exemplary substituted or unsubstituted $C_2$-$C_{10}$ alkenylene may be ethenylene, 1,2- or 1-3-propenylene, 1,4-but-2-enylene, or the like, or a combination comprising at least one of the foregoing. In addition, an exemplary substituted or unsubstituted $C_2$-$C_{10}$ alkynylene may be ethynylene, 1,3-propynylene, 1,4-but(-1- or -2-)ynylene, or the like, or a combination comprising at least one of the foregoing.

$Y_3$ is a group represented by

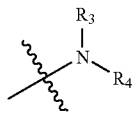

where $R_3$ and $R_4$ are each independently hydrogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or the like, or a combination comprising at least one of the foregoing, or $R_3$ and $R_4$ are bound to each other to form an alicyclic or aromatic ring. Where $R_3$ or $R_4$ is substituted, the substituent may be halogen, a primary, secondary or tertiary amino group, or the like, or a combination comprising at least one of the foregoing. an exemplary alicyclic ring may be a 3- to 8-membered cycloalkyl or cycloalkene ring. An exemplary aromatic ring may be a 6- to 8-membered aromatic ring. $Y_3$ may be —NH$_2$, —NH(CH$_3$), —NH(CH$_2$CH$_3$), or the like, or a combination comprising at least one of the foregoing.

Also, $Y_3$ is a group that is represented by

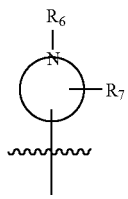

and has a 4- to 8-membered alicyclic ring or a 6- to 8-membered aromatic ring where $R_6$ and $R_7$ are each independently hydrogen, halogen with a proviso that $R_6$ is not halogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing. Where $R_6$ and $R_7$ are themselves substituted, the substituent may be halogen. $Y_3$ may be

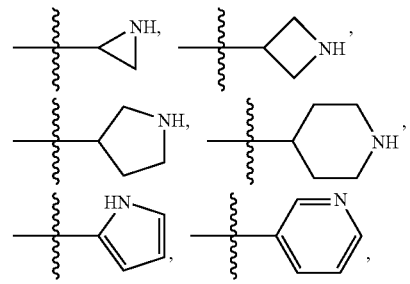

or the like, or a combination comprising at least one of the foregoing.

$R_8$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing. Where $R_8$ is substituted, an exemplary substituent may be halogen.

$R_9$ and $R_{10}$ are each independently hydrogen, halogen, a substituted or unsubstituted $C_1$-$C_{10}$ alkyl, a substituted or unsubstituted $C_3$-$C_{10}$ cycloalkyl, a substituted or unsubstituted $C_2$-$C_{10}$ alkenyl, a substituted or unsubstituted $C_2$-$C_{10}$ alkynyl, or a combination comprising at least one of the foregoing. Where $R_9$ and $R_{10}$ are substituted, an exemplary substituent may be halogen.

The bi-functional compound comprising A and B has a degree of polymerization of about 2 to about 30,000, specifically about 2 to about 20,000, and more specifically about 2 to about 10,000.

The compound comprising A and B may be a group represented by —$X_3$—$R_{13}$—$Y_3$ where $R_{13}$ is a $C_1$-$C_{10}$ alkylene, a $C_3$-$C_{10}$ cycloalkylene, a $C_2$-$C_{10}$ alkenylene, a $C_2$-$C_{10}$ alkynylene, or a combination comprising at least one of the foregoing, each group is substituted with at least one group of —COOH, —SO$_3$H, —SO$_2$H, —SOH, —H$_2$PO$_4$, —HPO$_4^-$, —PO$_4^{2-}$, or a combination comprising at least one of the foregoing, and $X_3$ and $Y_3$ are each the same as defined above.

In an embodiment, for the bi-functional compound comprising monomer(s) having A and B substituents, B may be derived from an amino acid including

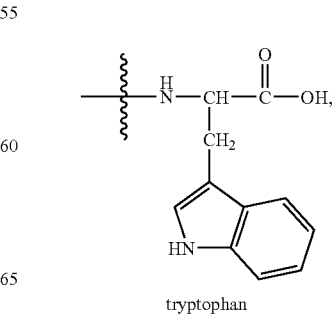

tryptophan

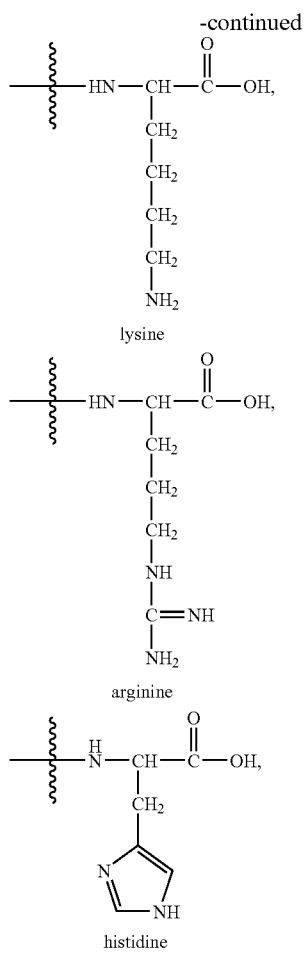

lysine arginine histidine or a combination comprising at least one of the foregoing.

In the bi-functional compound according to one or more embodiments, in which the bi-functional compound is ionized at a first and second pH, the first pH may be about 2 to about 5, specifically greater than 2 to less than 5, more specifically about 3 to about 4.5, and still more specifically about 3.5 to about 4.5; and the second pH may be about 7 to about 12, specifically about 7 to about 11, more specifically about 8 to about 11, and still more specifically about 8 to about 10.

The bi-functional compound of Formula I may be prepared by, in an embodiment, reacting a dianhydride or polyanhydride with a compound having a functional group that can react with the dianhydride. In an embodiment, the compound comprises two or more functional groups. Exemplary functional groups include hydroxy, phenoxy, thiol, amino, amido, imido, and the like, and combinations of the foregoing groups. In a specific embodiment, the compound is a nitrogen-containing compound having an amino group.

Exemplary dianhydrides include 1,2,4,5-benzenetetracarboxylic acid dianhydride (pyromellitic dianhydride), 3,3',4,4'-biphenyltetracarboxylic dianhydride, 2,2',3,3'-biphenyltetracarboxylic dianhydride, 2,3,3',4'-biphenyltetracarboxylic dianhydride, 1,2,4,5-benzenetetracarboxylic dianhydride, 3,3',4,4'-benzophenonetetracarboxylic dianhydride, 2,2',3,3'-benzophenonetetracarboxylic dianhydride, 2,3,3',4'-benzophenonetetracarboxylic dianhydride, bis(3,4-dicarboxyphenyl)ether dianhydride, bis(3,4'-dicarboxyphenyl)sulfone dianhydride, 1,4,5,8-naphthalenetetracarboxylic dianhydride, 1,2,5,6-naphthalenetetracarboxylic dianhydride, 2,3,6,7-naphthalenetetracarboxylic dianhydride, 2,2'-bis(3,4-dicarboxyphenyl)-hexafluoropropane dianhydride, cyclobutanetetracarboxylic dianhydride, methylcyclobutanetetracarboxylic dianhydride and 1,2,3,4-tetracarboxybutane dianhydride. In an exemplary embodiment, the dianhydride may be pyromellitic dianhydride having the structure:

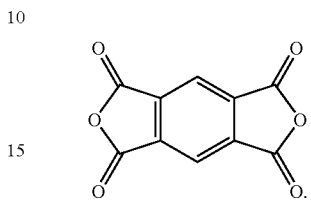

In one or more embodiments, the nitrogen-containing compound has one or more amino group, and where more than one group is present, may be heterobifunctional. Exemplary compounds having an amino functional group may include ethylenediamine, propylenediamine, trimethylenediamine, diethylenetriamine, triethylenetetraamine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis(3-aminopropyl)amine, 3-methoxyhexamethylenediamine, 1,2-bis(3-aminopropoxy)ethane, bis(3-aminopropyl)sulfide, 1,4-cyclohexanediamine, bis-(4-aminocyclohexyl)methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, tryptamine, 4-aminomethylpyridine, 1-(2-aminoethyl)imidazole, 1-(3-aminopropyl)imidazole, 1-(4-aminobutyl)imidazole, 1-(5-aminopentyl)imidazole, 1-(6-aminohexyl)imidazole, 3,3'-dimethylbenzidine, 3,3'-dimethoxybenzidine, 1,5-diaminonaphthalene, bis(4-aminophenyl)methane, bis(2-chloro-4-amino-3,5-diethylphenyl)methane, bis(4-aminophenyl)propane, 2,4-bis(b-amino-t-butyl) toluene, bis(p-b-amino-t-butylphenyl)ether, bis(p-b-methyl-o-aminophenyl)benzene, bis(p-b-methyl-o-aminopentyl)benzene, 1,3-diamino-4-isopropylbenzene, bis(4-aminophenyl) sulfide, bis(4-aminophenyl)sulfone, bis(4-aminophenyl)ether, 1,3-bis(3-aminopropyl)tetramethyldisiloxane. Amine-based amino acids may also be used, such as for example histidine, lysine, arginine, proline, and tryptophan. Polyamines, including linear, branched, hyperbranched, or dendrimeric polyamines, may also be used. Mixtures comprising at least one of these compounds may also be present. In an exemplary embodiment, the compound is ethylene diamine, 4-aminomethylpyridine, 1-(3-aminopropyl)imidazole), histidine, lysine, arginine, or a combination comprising at least one of the foregoing.

The bi-functional compound comprising A and B may be prepared by, for example, hydrolyzing a polyanhydride to form a carboxylic acid group, followed by activation of a resulting carboxylic acid group by reacting the carboxylic acid group with a material such as, N-hydroxysuccinimide ("NHS") in the presence of a dehydrating agent such as dicyclohexylcarbodiimide or 1,[3-(dimethylamino)propyl]-3- ethylcarbodiimide and an organic amine base (e.g., triethylamine) to form an activated intermediate compound having an ester bond (where in the case of N-hydroxysuccinimide, the activated intermediate compound is an NHS ester), and then coupling-reacting the so-activated carboxyl group with compound A (for example, H$_2$O) or compound B (for example, 1-(3-aminopropyl)imidazole). In another embodiment, after hydrolyzing the polyanhydride, the coupling-reacting may be carried out directly between the hydrolyzed polyanhydride and compound A or B in the presence of a dehydrating agent such as for example dicyclohexylcarbodiimide or 1,[3-(dimethylamino)propyl]-3-ethylcarbodiimide, and a catalyst (e.g., N,N-dimethylaminopyridine or 4-pyrrolidinopyridine).

Exemplary polyanhydrides include, for example, poly(ethylene-alt-maleic anhydride, styrene-alt-maleic anhydride, (styrene-alt-maleic anhydride)-co-styrene diblock copolymer, styrene-acrylate-maleic anhydride terpolymers, and the like, or a combination comprising at least one of the foregoing. In an exemplary embodiment, the polyanhydride is poly(ethylene-alt-maleic anhydride). It should be noted that these polyanhydrides are exemplary and should not be considered as limited thereto.

In an embodiment, the polyanhydride has a weight average molecular weight (Mw) of 100,000 to 500,000, specifically 125,000 to 475,000, more specifically 150,000 to 450,000, and still more specifically 150,000 to 400,000.

Alternatively, the compound comprising A and B may be prepared by directly reacting a polyanhydride (for example, poly(ethylene-alt-maleic anhydride, having an Mw of 100,000 to 500,000) with a reactant comprising A (for example, H$_2$O) or a reactant comprising B (for example, 1-(3-aminopropyl)imidazole). In this regard, a net charge of the compound comprising A and B may be adjusted by having A or B contained in the compound at an appropriate ratio in the reaction.

In an embodiment, a solid support on which a bi-functional compound is immobilized can therefore be prepared by sequentially reacting a substrate, a surface treatment agent, a dianhydride or polyanhydride, and a nitrogen-containing compound, wherein the bi-functional compound immobilized on the substrate is positively charged at a first pH and negatively charged at a second pH. The resulting reaction product is a solid support having a bi-functional compound immobilized thereon.

One or more embodiments include a solid support in which the compound described above is immobilized on a surface thereof. In an embodiment, the solid support comprises a substrate and the bi-functional compound.

The substrate of the solid support on which the compound is immobilized may have the form of, for example, a planar plate, a multilayered structure, a non-planar structure such as sphere, bead, sieve or pillar, or a surface in a microchannel, but is not limited to these. Where the surface of each of these substrates has additional features or textures for increasing surface area, the features may include pits, holes, posts, grooves, linear or nonlinear lines and spaces, and the like, and combinations of the foregoing. In an embodiment, the solid support may have a shape of the surface of the microchannel in a microfluidic device.

The substrate of the solid support on which the compound is to be immobilized may be glass, magnetic beads, silica, fused silica, polyethylene, polypropylene, polycarbonate, polyester, polyimide, slide glass, silicon, TiO$_2$, Al$_2$O$_3$, SiN$_X$, TiN$_X$, sapphire, metals such as steel, aluminum, titanium, tantalum, silver, gold, platinum, substrates such as SiO$_2$ or silicon coated with one of these metals, or the like, or a combination comprising at least one of the foregoing. The foregoing embodiments should be considered exemplary and should not be considered as limited thereto.

The solid support may be prepared by activating a terminal portion of a chain of the compound with an activator comprising an active group such as an aldehyde, an anhydride including mixed anhydride, an acid halide, or an activated ester group (e.g., an NHS ester), and coupling the activated compound with a solid support previously treated to have a functional group, such as an amino group, on the surface. The activation of the compound and the solid support may be performed using any known method. For example, the compound may be activated by oxidizing a terminal group of the compound, or by coupling the compound with an ester compound, an aldehyde, an acid halide, or an anhydride to introduce an active group into the compound.

The solid support may be treated with a surface-treating agent that affixes to the surface of the solid support, and provides a free nitrogen-containing group to allow attachment of the activated carboxylic acid group. In an embodiment, the surface treating agent is heterobifunctional and provides at one end a nitrogen-containing functional group, such as an amine, and at the other end, a reactive group that can react to form a covalent bond to the surface of the solid support. In another embodiment, the solid support may be treated with a surface treating agent having an isocyanate or isothiocyanate-containing group, and at the other end, a reactive group that can react to form a covalent bond to the surface of the solid support. In an embodiment, where an isocyanate or isothiocyanate is used, the bifunctional compound immobilized on the treated surface of the solid support may be an amine-containing polymer, or a phenol-containing polymer, where immobilization of such polymers may be accomplished via a urea or urethane link. In another embodiment, it will be appreciated that an isocyanate or isothiocyanate surface-treating agent may be further treated with, for example, ammonia, or a polyfunctional amine to provide additional amine or other functional groups for reaction with the activated compound.

Exemplary surface treating agents include, but are not limited to, aminosilanes such as 3-aminopropylsilane, 3-aminopropylmethoxysilane, 3-aminopropyldimethoxysilane, 3-aminopropyldimethylsilane, 3-aminopropyl(methoxydimethylsilane), 3-aminopropyl(trimethoxysilane), 3-aminopropyl(triethoxysilane), 3-aminopropyl(triisopropoxysilane), 3-aminopropyl(tributoxysilane), 3-isocyanatopropylsilane, 3-isocyanatopropyl(trimethoxysilane), 3-isothiocyanatopropylsilane, 3-isothiocyanatopropyl(trimethoxysilane), or the like, or a combination comprising at least one of the foregoing.

The solid support may be activated by coating a surface of the solid support with an active material such as an aminosilane by a conventional coating technique (e.g., dip coating, spin coating, and the like, but not limited to these). Alternatively, the solid support on which the compound is immobilized may be prepared by coating an activated substrate with the polyanhydride as described above (for example, poly(ethylene-alt-maleic anhydride having an Mw of 100,000-500,000), hydrolyzing an anhydride moiety of the polyanhydride coated on the substrate to expose a carboxylic acid group, reacting the carboxylic acid group with N-hydroxysuccinimide in the presence of dicyclohexane carbodiimide or 1,[3-(dimethylamino)propyl]-3-ethylcarbodiimide in the presence of an amine base to activate the carboxyl group by forming the NHS ester, and then coupling-reacting the activated carboxylic acid group with a reactant comprising A (for example, H₂O) or the reactant comprising B (for example, 1-(3-aminopropyl)imidazole).

One or more embodiments include a method of isolating a nucleic acid by with the compound and the solid support on which the compound is immobilized, the method including: contacting the compound or the solid support on which the compound is immobilized with a sample comprising a nucleic acid at a first pH; and exposing the compound with the nucleic acid bound thereto to a solution with a second pH that is higher than the first pH, to release the nucleic acid.

In an embodiment, the method of isolating the nucleic acid includes contacting the compound or the solid support on which the compound is immobilized with the sample comprising the nucleic acid at the first pH. The sample may be a biological or non-biological sample comprising a nucleic acid, for example, blood lysate, cell lysate, polymerase chain reaction ("FOR") products, or a combination comprising at least one of the foregoing. The compound and/or the solid support on which the compound is immobilized are as described hereinabove. In an embodiment, the first pH may be about 2 to about 5, specifically greater than or equal to 2 to less than 5, more specifically about 3 to about 4.5, and still more specifically about 3.5 to about 4.5.

In an embodiment, the method of isolating the nucleic acid includes exposing the compound, for example, the compound on the solid support, and having the nucleic acid bound thereto, to the solution having a second pH higher than the first pH, to release the nucleic acid. The second pH may be about 7 to about 12, specifically about 7 to about 11, more specifically about 8 to about 11, and still more specifically about 8 to about 10. A solution for eluting the nucleic acid may include water or an appropriate aqueous buffer. An example of an aqueous buffer is a tris-hydroxymethyl aminomethane-ethylene diamine tetraacetic acid buffer (Tris-EDTA buffer). Exposing of the compound to the buffer may be performed at room temperature or at a temperature higher than room temperature, for example, at a temperature of 50 to 95° C.

In an embodiment, where an aqueous buffer solution is used for exposing the compound, the total buffer concentration is 0.001 to 10M, specifically 0.01 to 5 M, and more specifically 0.1 to 2 M.

An exemplary method of forming a surface immobilized compound on a solid support, according to an embodiment, is shown below. In the exemplary method shown in Reaction Scheme 1:

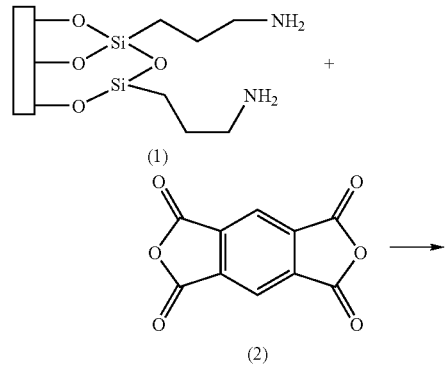

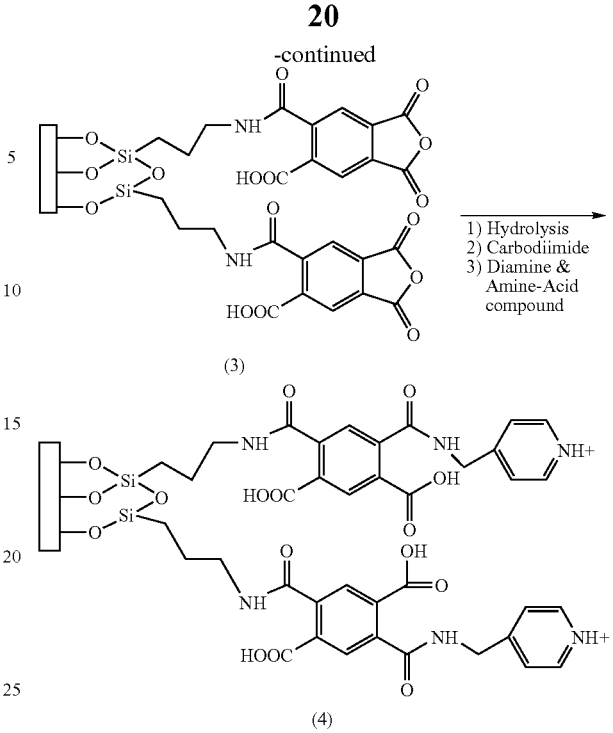

a treated surface (1) (e.g., silicon dioxide) previously treated with a surface treating agent (e.g., 3-aminopropyltriethoxysilane), is then reacted with a dianhydride (e.g., pyromellitic dianhydride (2)) to form anhydride intermediate (3). Intermediate (3) is then hydrolyzed, and the resulting free acid groups reacted with a diamine (e.g., 4-aminomethylpyridine) in the presence of a dehydrating agent (a carbodiimide, such as 1,[3-(dimethylamino)propyl]-3-ethylcarbodiimide) to form the bifunctional material (4).

Another exemplary method of forming a surface immobilized compound on a solid support, according to an embodiment, is shown below. In the exemplary method shown in Reaction Scheme 2:

Reaction Scheme 2:

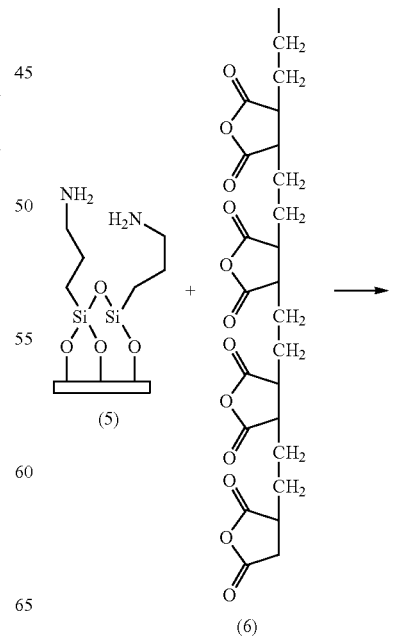

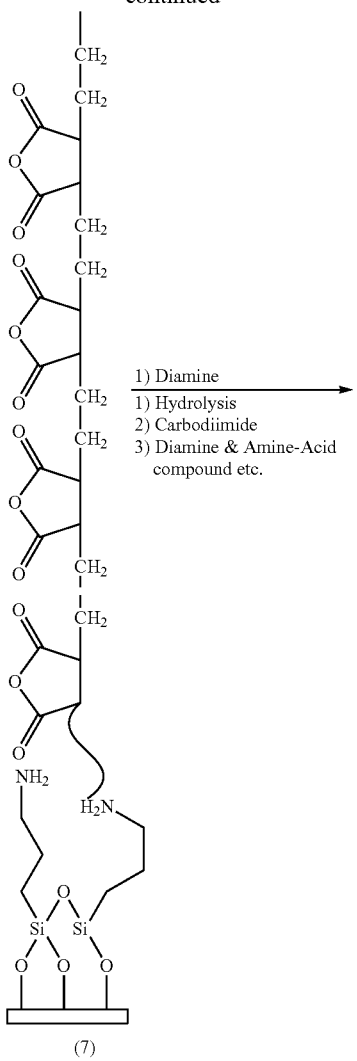

(7)

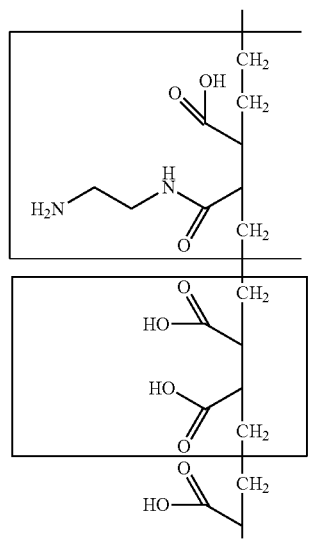

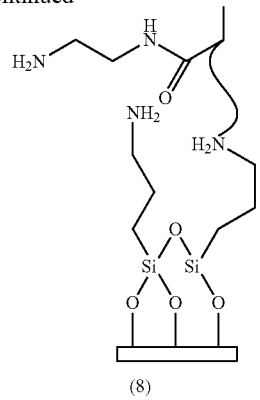

(8)

a treated surface (5) (e.g., silicon dioxide) previously treated with a surface treating agent (e.g., 3-aminopropyltriethoxysilane), is then reacted with a polymeric anhydride (e.g., poly(ethylene-alt-maleic anhydride (6)) to form anhydride intermediate (7). Intermediate (7) is then hydrolyzed, and the resulting free acid groups reacted with a diamine (e.g., ethylene diamine as shown) in the presence of a dehydrating agent (a carbodiimide, such as 1,[3-(dimethylamino)propyl]-3-ethylcarbodiimide) to form the bifunctional material (8).

It will be appreciated that the above exemplary processes are for illustrative purposes and should not be construed as limiting thereto.

Hereinafter, one or more embodiments will be described in detail with reference to the following examples. However, these examples are included as exemplary are not intended to limit the purpose and scope of the invention.

EXAMPLE 1

Synthesis of Bi-functional Material Positively Charged at a First pH and Negatively Charged at Second pH on Silicon Substrate, and Analysis Thereof (1) Preparation of Bi-functional Material that is Positively Charged at First pH and Negatively Charged at Second pH.

A silicon wafer substrate (25 mm×25 mm, with silicon dioxide deposited thereon to a thickness of about 1,000 angstroms) is immersed in a solution of 100 mM 3-aminopropyltriethoxysilane in ethanol, and incubated at room temperature for about 1 hour. The silicon substrate so treated was washed using anhydrous ethano to provide a silicon substrate with amino groups introduced on its surface. The silicon substrate having the amino groups so introduced is next immersed in a solution of 200 mM poly(ethylene-alt-maleic anhydride) having an Mw of 100,000 to 500,000, and a degree of polymerization n=900 to 4,000) based on a repeating unit of ethylene-maleic anhydride in N-methyl-2-pyrrolidone ("NMP") and incubated at room temperature for 1 hour. Poly(ethylene-alt-maleic anhydride thus reacts with the amino groups present on the surface of the silicon substrate, and are immobilized on the silicon substrate. Subsequently, samples of the silicon substrate so treated is alternately washed with N-methyl-2-pyrrolidone (NMP) and ethanol, and dried.

Samples of the dried silicon substrate are then immersed in either a.) a solution of 400 mM ethylenediamine and 600 mM water in NMP, or b.) a solution of 400 mM 4-aminomethylpyridine and 600 mM water in NMP, and is incubated at room temperature in each solution for 1 hour. Thereafter, the silicon substrates are washed with ethanol and dried. As a result, two types of silicon substrate, each of which was coated with a bi-functional material (sample (a), having ethylene diamine and hydroxy groups; and sample (b), having 4-aminomethylpyridine and hydroxy groups), are prepared.

(2) Analysis of the Silicon Substrate Coated with the Bi-functional Material Prepared from the Solution of 400 mM of Ethylenediamine and 600 mM of Water in NMP (Sample (a).

X-ray photoelectron spectroscopy ("XPS") analysis was performed on the silicon substrate coated with the bi-functional material prepared from the solution of 400 mM of ethylenediamine and 600 mM of water in NMP (sample (a), as described in (1) above) in order to determine the presence of functional groups on the surface of the silicon substrate. A Physical Electronics Quantum2000 microprobe with a monochromated A1Kα X-ray source (hυ=1486.6 eV) was used as the XPS device. Functional groups corresponding to ethylene diamine and hydroxy were found to exist on the surface of the silicon substrate.

In the XPS spectra obtained from the analysis, the nitrogen 1 s orbital peak appearing at 400 eV, and representing the binding energy for a primary amino group, showed a greater intensity in the XPS spectra for the silicon substrate coated with the bi-functional material than was seen in the XPS spectra on the silicon substrate coated only with 3-aminopropyltriethoxysilane. This result shows that the bi-functional material has a plurality of surface-bound primary amino groups as provided by the above method.

In addition, the magnitude of the carbon 1 s orbital peak appears at 285 eV, at a binding energy representing carbon that is directly bound to a primary amino group. The observed intensity is significantly greater in XPS spectra for the silicon substrate coated with the bi-functional material than for the XPS spectra of the silicon substrate coated with 3-aminopropyltriethoxysilane. This result shows that the bi-functional material has carbon that is directly bound to a plurality of primary amino groups.

In addition, a carbon 1 s orbital peak also appears at 288 eV, a binding energy representing a carbonyl (C=O) group, has a greater intensity in XPS spectra for the silicon substrate coated with the bi-functional material, than seen in the XPS spectra for the silicon substrate coated with 3-aminopropyltriethoxysilane. This result thus further shows that the bi-functional material has an associated carbonyl group.

From the results above, it is thus qualitatively confirmed that the bi-functional material, which has an amino group and a carbonyl group, including a carbonyl group connected to a hydroxy (—OH) group, is coated on the silicon substrate by the above method.

(3) Analysis of the Silicon Substrate Coated with the Bi-functional Material Prepared from the Solution of 400 mM of 4-Aminomethylpyridine and 600 mM of Water in NMP (Sample (b)).

Time-of-flight secondary ion mass spectrometry ("TOF-SIMS") analysis is performed on the silicon substrate coated with the bi-functional material prepared from the solution of 400 mM of 4-aminomethylpyridine and 600 mM of water in NMP (sample b, as described in Experiment (1) above), to analyze a surface of the silicon substrate. A TOF-SIMS V apparatus (available from ION-TOF GmbH, Germany) emitting 15 kV Ga radiation (average current: 1 pA, pulse time: 200 μs) was used as a TOF-SIMS apparatus.

In the data, a peak (m/z=79) representing pyridine is observed, showing that the surface of the silicon substrate is coated with a material having pyridine. In addition, by XPS analysis as described above, it can also be shown that a carbonyl group is present on the surface of the silicon substrate, and the carbonyl group includes a carbonyl group having a hydroxy (—OH) group.

Thus, the bi-functional material, having both a pyridine group and a carbonyl group, where the carbonyl group includes a carbonyl group having an —OH group, is coated on the silicon substrate.

EXAMPLE 2

Isolation of Genome DNA by Using Bi-functional Material that is Positively Charged at First pH and Negatively Charged at Second pH (1) Preparation of Bi-functional Material that is Positively Charged at First pH and Negatively Charged at Second pH.

Poly(ethylene-alt-maleic anhydride) (Mw 100,000 to 500,000; degree of polymerization n=900 to 4,000 is immobilized on a magnetic bead coated with an amino group (available from Invitrogen, under the trade name of Dyanl AS DYNABEADS® M-270 Amine, $2 \times 10^9$ beads/ml, with a diameter of 2.8 μm), and the magnetic bead is reacted with 1-(3-aminopropyl)imidazole to prepare a material having a carboxyl group and an imidazole group, capable of having a positive charge at a first pH of 2 to 5, and negative charge at a second pH of 7 to 12.

First, the magnetic bead coated with the amino group is immersed in a solution of 200 mM the above-mentioned poly(ethylene-alt-maleic anhydride) based on the repeating unit of ethylene-maleic anhydride, in N-methyl-2-pyrrolidone (NMP) is incubated at room temperature for 1 hour. Next, poly(ethylene-alt-maleic anhydride) is reacted with the amino group on the magnetic bead and thereby immobilized on the magnetic bead. After this reaction, the magnetic bead is washed with ethanol and dried.

Next, the magnetic bead with the polyanhydride (poly(ethylene-alt-maleic anhydride) immobilized thereon was added to a solution of 400 mM of 1-(3-aminopropyl)imidazole and 600 mM of water in N-methyl-2-pyrrolidone (NMP) and incubated at room temperature for 1 hour. Then, the magnetic bead was washed with ethanol. In this way, a material with a carboxyl group and an imidazole group, is prepared. The prepared material was washed with ethanol and dried.

The material so prepared is a bi-functional compound that is bound to at least one monomer monomers represented by formulae M0, M1, M2, and M3 below and comprises at least one of a monomer with A and at least one of a monomer with B,

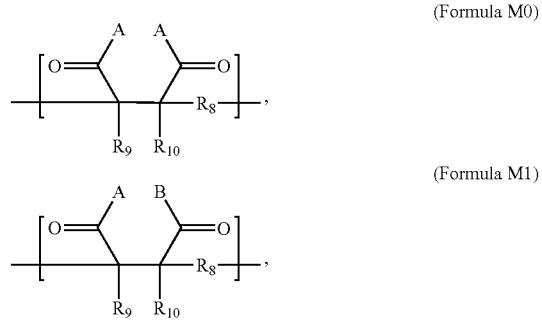

-continued

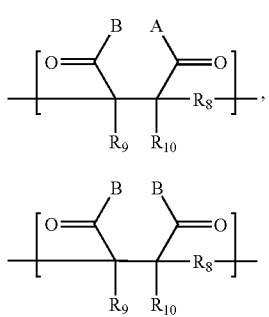

wherein A is —OH, B is a compound represented by

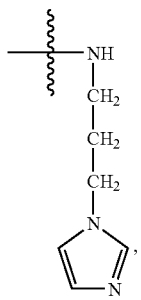 [SMILES: *NCCCn1ccnc1]

$R_8$ is ethyl, and $R_9$ and $R_{10}$ are each independently hydrogen. It is noted that for present purposes, the structure of monomer units of M1 and M2 are interchangeable.

Characterization of the magnetic bead was performed as described in Example 1 above, by XPS and TOF-SIMS analysis to confirm the surface composition of the magnetic bead having the bi-functional compound immobilized thereon. Thus, in the XPS analysis, it is seen that the prepared compound has a carbonyl group, and the carbonyl group includes a carbonyl group having a hydroxyl (—OH). In addition, in the TOF-SIMS analysis, it is seen that the bi-functional compound has an imidazolyl group.

(2) Isolation of Genome DNA by Using Bi-functional Material

*E. coli* genome DNA was isolated using the magnetic bead with the bi-functional material prepared in (1) above immobilized thereon.

*E. coli* in phosphate buffered saline solution ("PBS") (0.1 $OD_{600}$) was thermally lysed by heating twice at each of 95° C. for 5 minutes and 0° C. for 1 minute.

Next, each of 10 μl ($2\times10^7$ beads), 30 μl ($6\times10^7$ beads), and 50 μl ($1\times10^8$ beads) of a solution of the magnetic bead with the bi-functional material prepared in (1) above immobilized thereon ($2\times10^9$ beads/ml, in distilled water) was taken, and each magnetic bead solution was exchanged with a binding buffer, 100 μl of a 100 mM sodium acetate buffer (pH 4). 100 μl of the magnetic bead solution and 50 μl of *E. coli* lysate were mixed together, and vortexed for 2 minutes. The magnetic beads were separated from the mixed solution with a magnet. The concentration of DNA in the solution from which the magnetic beads were removed was measured using a NANODROP™ ND1000 apparatus (obtained from Thermo Scientific).

The separated magnetic beads were suspended in a 10 mM Tris-HCl buffer, pH 7, and vortexed for 1 minute. The magnetic beads were separated from the solution by using a magnet, and washed.

The washed magnetic beads were suspended in a 100 mM Tris-HCl buffer, pH 9, and incubated at 80° C. for 4 minutes while vortexing was performed for 5 seconds every 30 seconds to elute a nucleic acid from the magnetic beads. Then, the magnetic beads were removed from the solution by using a magnet to obtain a solution comprising an isolated genome DNA. The amount of nucleic acid in the obtained solution was quantified using a NANODROP™ ND1000 apparatus.

Table 1 shows a binding efficiency of the nucleic acid in *E. coli* lysate to the magnetic beads with the bi-functional material prepared in (1) above immobilized thereon and an elution efficiency of the nucleic acid from the magnetic beads.

TABLE 1

| Bead number | Binding efficiency (%) | Elution efficiency (%) |
|---|---|---|
| $2 \times 10^7$ | 88.4 ± 1.6 | 99.2 ± 5.6 |
| $6 \times 10^7$ | 93.8 ± 0.9 | 95.8 ± 6.8 |
| $1 \times 10^8$ | 99.2 ± 1.3 | 80.4 ± 3.3 |

In Table 1, the binding efficiency and the elution efficiency are respectively defined as the DNA binding amount/amount of DNA existing in lysate solution×100, and the DNA elution amount/DNA binding amount×100.

(3) Isolation of Genome DNA by Using Bi-functional Material: Effect of Binding Buffer pH A 100 mM sodium acetate buffer used as a binding buffer is varied to have a pH of 3, 4, or 5, and elution is performed at each pH by incubating the magnetic beads having the bound DNA in buffer at 65° C. for 2 minutes. The number of magnetic beads used was $6\times10^7$ per ml; otherwise, the experimental processes were performed in the same manner as in (2) above.

Table 2 shows, according to a change in pH, the binding efficiency of the nucleic acid in *E. coli* lysate to the magnetic beads with the bi-functional material prepared in (1) above immobilized thereon, elution efficiency of the nucleic acid from the magnetic beads, and yield.

TABLE 2

| Binding buffer pH | Binding efficiency (%) | Elution efficiency (%) | Yield (%) |
|---|---|---|---|
| 3 | 99.0 | 69.0 | 68.3 |
| 4 | 95.5 | 83.2 | 79.5 |
| 5 | 34.0 | 88.0 | 29.9 |

In Table 2, the binding efficiency and the elution efficiency are the same as defined in those of Table 1, and the yield (%) is defined as binding efficiency×elution efficiency.

From the results of Table 2, it was confirmed that at pH 5 or less, the lower the pH, the greater the binding efficiency, and at pH 5 or less, the higher the pH, the greater the elution efficiency. As a result, as the pH increases from 3 to 5, the yield was increased and then decreased.

(4) Effect of Elution Buffer pH

The effect of the pH of the elution buffer was determined in the same manner as in (2) above, except that a 100 mM sodium acetate buffer with a pH 4 was used as a binding buffer, and the pH of the elution buffer was varied as described below. The number of magnetic beads used was $6\times10^7$ per ml.

The elution buffer used was either a 100 mM Tris-HCl solution at pH 7, a 100 mM Tris-HCl solution at pH 9, or a 100 mM sodium carbonate solution at pH 11.

Table 3 shows how change in pH affects elution efficiency. The elution efficiency is as defined above.

TABLE 3

| Elution pH | 7 | 8 | 11 |
|---|---|---|---|
| Elution efficiency (%) | 70.5 | 83.2 | 91.2 |

From the results of Table 3, it can be seen that elution is efficiently performed at pH 7 or more. After a supplementary experiment was performed, it was demonstrated that elution was efficiently performed even at pH 12.

EXAMPLE 3

Isolation of Genome DNA by Using Material that is Positively Charged at First pH and Negatively Charged at Second pH Bi-functional compounds having histidine, lysine and arginine moieties were prepared, and genome DNA was isolated using these bi-functional compounds.

(1) Preparation of Bi-functional Compound Having a Histidine Moiety

Experimental Group 1: silica bead on which a bi-functional material having a pyridyl group is immobilized. A silica bead having an average diameter of about 14 μm is immersed in a solution of 100 mM of 3-aminopropyltriethoxysilane in ethanol and incubated at room temperature for 1 hour. Then, the silica bead is washed using anhydrous ethanol to prepare a silica bead to which an amino group was introduced. Thereafter, the thus-obtained silica bead with the amino group on its surface is immersed in a solution of 200 mM of poly(ethylene-alt-maleic anhydride having an average molecular weight of 100,000 to 500,000, and a degree of polymerization n=900 to 4,000, based on a repeating unit of ethylene-maleic anhydride, in N-methyl-2-pyrrolidone (NMP) and incubated at room temperature for 1 hour. After the incubating, the silica bead is alternately washed using pure N-methyl-2-pyrrolidone (NMP) and ethanol and then dried. Thus, a silica bead on which poly(ethylene-alt-maleic anhydride is immobilized, is obtained.

Then, the silica bead so obtained is immersed in a solution of 400 mM of 4-aminomethylpyridine and 600 mM of water in NMP and incubated at room temperature for 1 hour. The silica bead is then washed with ethanol and dried.

Experimental Group 2: silica bead on which a bi-functional material having a histidine moiety is immobilized. A silica bead with a bi-functional material having a histidine moiety immobilized thereon is prepared as follows. First, the prepared silica bead on which poly(ethylene-alt-maleic anhydride) are immobilized is immersed in a solution of 100 mM 4-morpholineethanesulfonic acid ("MES") at pH 6 in distilled water and incubated for 4 hours to hydrolyze the polyanhydride, then dried. Then, the dried silica bead are immersed in a solution of 100 mM of 1-ethyl-3-(3-dimethylaminopropyl)carbodiimide hydrochloride ("EDC") and 200 mM of N-hydroxysuccinimide (NHS) in ethanol with 10% MES (v/v) included, and incubated at room temperature for 30 minutes. Then, the silica bead was washed using water and ethanol in this order and dried. In this way, a silica bead having an activated carbonyl group was obtained. The dried silica bead is then immersed in a solution of 200 mM of histidine in 100 mM phosphate buffered saline (PBS), pH 7.4 and incubated at room temperature for 2 hours. Then, the silica bead is washed with water and ethanol in this order and dried.

The compound synthesized on the silica bead, as Experimental Group 2, is a bi-functional compound that is bound to at least one monomer monomers represented by Formulae M0, M1, M2, and M3 below and comprises at least one of a monomer with A and at least one of a monomer with B,

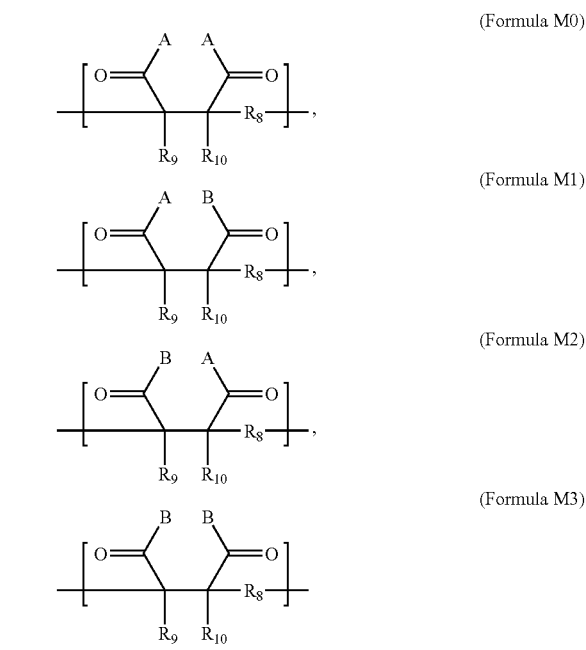

wherein A is —OH,
B is

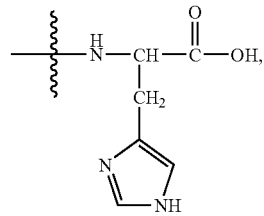

$R_8$ is ethyl, and $R_9$ and $R_{10}$ are each independently hydrogen. It is noted that for present purposes, the structure of monomer units of M1 and M2 are interchangeable.

The presence of a carbonyl group including the carbonyl group that is directly bound to —OH, and the histidine moiety on the silica bead are confirmed using XPS and TOF-SIMS analyses.

(2) Isolation of Genome DNA by Using the Prepared Silica Bead

Genome DNA was isolated using the silica beads prepared in (1) above as Experimental Groups 1 (4-aminomethylpyridine) and 2 (histidine).

First, 0.01 g of each of the silica beads of Experimental Groups 1 and 2, 70 μl of 100 mM sodium acetate, pH 3 (binding solution), and 140 μl of purified E. coli genome DNA (28 ng/μl in distilled water) is mixed while being tumbled for 3 minutes. The mixture is rotated at 1000 rpm for 1 minute and then a supernatant removed from the mixture.

210 μl of 10 mM Tris-HCl at pH 7.4 as a washing buffer is added to the separated silica bead, and the resultant is mixed while being vortexed for 1 minute. The mixture is rotated at 1,000 rpm for 1 minute, and supernatant is removed. 210 μl of a Tris-EDTA ("TE") buffer (100 mM Tris-HCl-EDTA at pH 8.2) as an elution buffer is added to the separated silica beads and the resultant incubated at 70° C. for 3 minutes.

The concentration of DNA in each step is measured using a NANODROP™ ND1000 apparatus, to determine binding efficiency, elution efficiency, and yield.

TABLE 4

| Silica Bead | Binding Efficiency (%) | Elution Efficiency (%) | Yield (%) |
|---|---|---|---|
| Experimental Group 1a[a] | 100 | 84.5 | 84.5 |
| Experimental Group 1b[a] | 98.3 | 80.1 | 78.7 |
| Experimental Group 2a[a] | 77.5 | 82.9 | 64.2 |
| Experimental Group 2b[a] | 77.9 | 85.7 | 66.8 |

[a]Note:
sub-designations a and b refer to repeat runs.

Each experiment was repeated twice. As seen in the data in Table 4, the yield of Experimental Group 1 (the 4-aminomethylpyridine-modified bead) is significantly greater, varying from 11.9% to 20.3% to 11.9% greater than the yield of Experimental Group 2 (the histidine-modified bead).

A second set of experiment was performed in the same manner as in the experiment described above, but using 0.02 g of the silica bead from Experimental Group 2 and as a binding solution, 200 mM sodium acetate at pH 3. Table 5 shows results of DNA isolation when the amount of silica bead and the concentration of binding solution were increased.

TABLE 5

| Silica Bead | Binding Efficiency (%) | Elution Efficiency (%) | Yield (%) |
|---|---|---|---|
| Experimental Group 2c[b] | 93.3 | 81.9 | 76.4 |
| Experimental Group 2d[b] | 85 | 82.7 | 70.3 |

[b]Note:
sub-designations c and d are repeat runs.

As shown in Table 5, the yield of Experimental Groups 2c and 2d vary from about 3.5 to 12.2% greater than Experimental Groups 2a and 2b in Table 4.

(3) Preparation of Silica Bead with Bi-functional Compound Having a Lysine or Arginine Moiety Immobilized Thereon and Isolation of Genome DNA Using the Same.

Silica bead on which a bi-functional compound having a lysine or arginine moiety was immobilized (respectively referred to as silica beads of Experimental Groups 3 and 4) was prepared according to the procedure described in Example (3), (1) above using lysine or arginine instead of histidine. The bi-functional compound is then evaluated for genome DNA binding and purification also as above, and is isolated in the same manner as in (2) above from the prepared silica beads for each of Experimental Groups 3 and 4.

TABLE 6

| Silica Bead | Binding Efficiency (%) | Elution Efficiency (%) | Yield (%) |
|---|---|---|---|
| Experimental Group 3 | 84.3 | 77.3 | 65.2 |
| Experimental Group 4 | 86.1 | 79.1 | 68.1 |

As seen in the data in Table 6 above, the yield for lysine (65.2%, Experimental Group 3) and arginine (68.1%, Experimental Group 4) is about the same as that observed for histidine (64.2% and 66.8% for Experimental Groups 2a and 2b, respectively; see Table 4). From the above, it can be seen that the highest overall yield is obtained from the 4-aminomethylpyridine modified beads, irrespective of buffer pH.

Thus, according to the one or more of the above embodiments, a nucleic acid can be efficiently isolated using a bi-functional material and a solid support with the bi-functional material immobilized thereon.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A bi-functional compound that is positively charged at a first pH and negatively charged at a second pH, the bi-functional compound represented by Formula I below:

$$Q\text{-}X\text{-}Q_1 \quad \text{(Formula I)}$$

wherein Q or $Q_1$

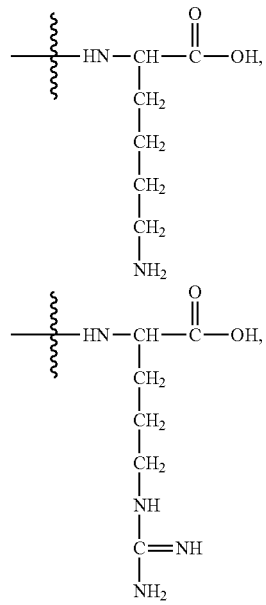

or a combination comprising at least one of the foregoing,

X is a compound represented by

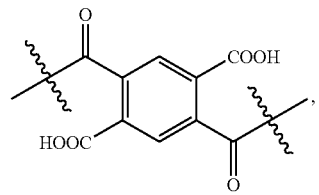

-continued

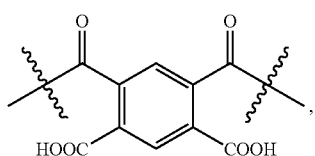

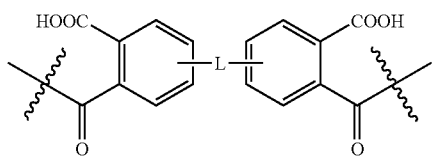

wherein L is a bond, —O—, —CO—, —S—, —SO$_2$—, —CH$_2$—, —C(CH$_3$)$_2$—, —C(CF$_3$)$_2$—, or a combination comprising at least one of the foregoing,

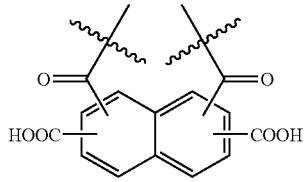

wherein the carbonyl group and the carboxyl group are substituted at any available carbon position except for a ring connection portion,

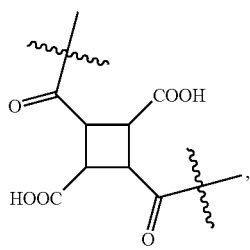

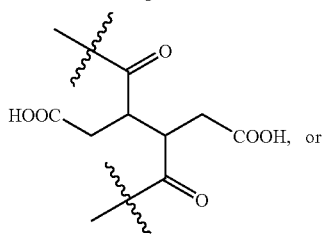

a combination comprising at least one of the foregoing, or wherein the bi-functional compound that is positively charged at a first pH and negatively charged at a second pH, wherein the bi-functional compound is linked to at least one monomer comprising monomers represented by M0, M1, M2, M3, or a combination comprising at least one of the foregoing, below, and wherein the bi-functional compound comprises at least one of a monomer with A and at least one of a monomer with B,

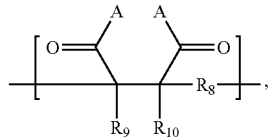
(Formula M0)

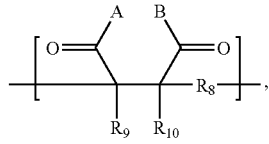
(Formula M1)

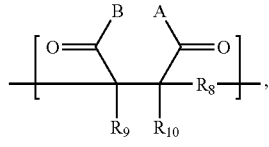
(Formula M2)

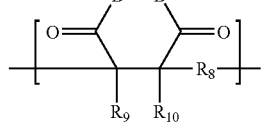
(Formula M3)

wherein A is a group represented by —OH or —X$_2$—R$_{11}$—Y$_2$— where X$_2$ is O—, —S—, —NR$_{12}$—, or a combination comprising at least one of the foregoing, where R$_{12}$ is hydrogen, halogen, a substituted or unsubstituted C$_1$-C$_{10}$ alkyl, or a combination comprising at least one of the foregoing, R$_{11}$ is a substituted or unsubstituted C$_1$-C$_{10}$ alkylene, a substituted or unsubstituted C$_3$-C$_{10}$ cycloalkylene, a substituted or unsubstituted C$_2$-C$_{10}$ alkenylene, a substituted or unsubstituted C$_2$-C$_{10}$ alkynylene, or a combination comprising at least one of the foregoing, and Y$_2$ is —COOH, —SO$_3$H, —SO$_2$H, —SOH, —H$_2$PO$_4$, —HPO$_4^-$, —PO$_4^{2-}$, or a combination comprising at least one of the foregoing, and B is

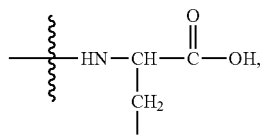

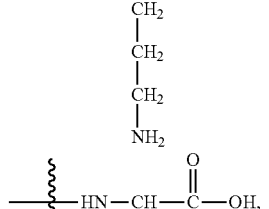

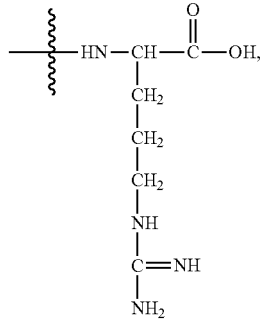

or a combination comprising at least one of the foregoing, and wherein the bi-functional compound comprising A and B has a polymerization degree of about 2 to about 30,000.

2. The bifunctional compound of claim 1 wherein the first pH is about 2 to about 5, and the second pH is about 7 to about 12.

3. A solid support on which a bi-functional compound is immobilized comprising:

a substrate, and bi-functional compound immobilized on the substrate, the bi-functional compound being positively charged at a first pH and negatively charged at a second pH, and represented by Formula I below:

Q-X-Q₁                                      (Formula I)

wherein Q or Q₁ is

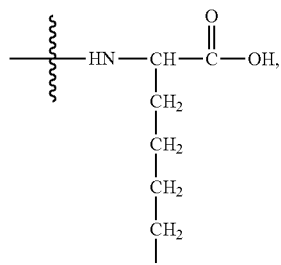

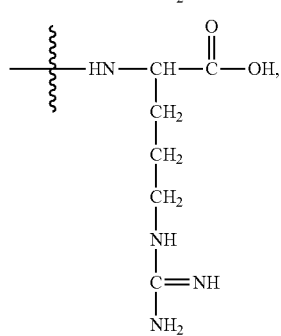

or a combination comprising at least one of the foregoing, or a bi-functional compound that is positively charged at a first pH and negatively charged at a second pH, wherein the bi-functional compound is linked to at least one monomer comprising monomers represented by Formulas M0, M1, M2, M3, or a combination comprising at least one of the foregoing, below, and wherein the bi-functional compound comprises at least one of a monomer with A and at least one of a monomer with B,

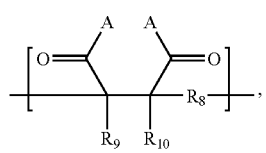
(Formula M0)

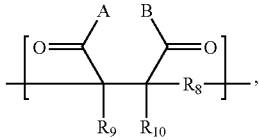
(Formula M1)

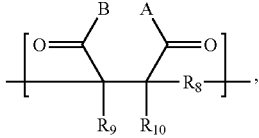
(Formula M2)

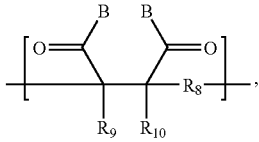
(Formula M3)

wherein A is a group represented by —OH or —$X_2$—$R_{11}$—Y2 where $X_2$ is O—, —S—, —$NR_{12}$—, or a combination comprising at least one of the foregoing, where $R_{12}$ is hydrogen, halogen, a substituted or unsubstituted $C_1$-$C_{10}$ alkyl, or a combination comprising at least one of the foregoing, $R_{11}$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing, and $Y_2$ is —COOH, —$SO_3H$, —$SO_2H$, —SOH, —$H_2PO_4$, —$HPO_4^-$, -$PO_4^{2-}$, or a combination comprising at least one of the foregoing, and B is

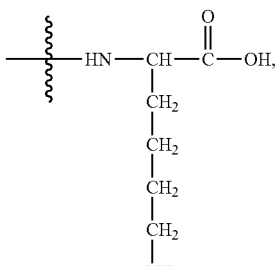

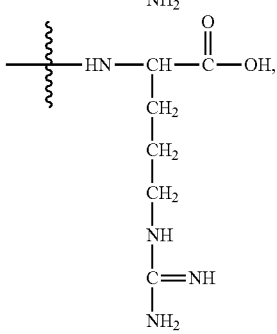

or a combination thereof, and wherein the bi-functional compound comprising A and B has a polymerization degree of about 2 to about 30,000.

4. The solid support of claim 3, wherein the first pH is about 2 to about 5, and the second pH is about 7 to about 12.

5. The solid support of claim 3, where the substrate is in the form of a planar plate, a multilayered structure, a non-planar structure including sphere, bead, sieve, pillar or combination comprising these, or a surface of a microchannel in a microfluidic device.

6. The solid support of claim 3, wherein substrate of the solid support on which the hi-functional compound is immobilized is glass, magnetic heads, silica, fused silica, polyethylene, polypropylene, polycarbonate, polyester, polyimide, slide glass, silicon wafer, $SiO_2$, $TiO_2$, $Al_2O_3$, $SiN_X$, $TiN_X$, sapphire, metals such as steel, aluminum, titanium, tantalum, silver, gold, platinum, $SiO_2$ or silicon substrates coated with one of these metals, oxides, or nitrides, or a combination comprising at least one of the foregoing.

7. The solid support of claim 6, where the surface of the substrate has additional features or textures for increasing surface area, the features comprising pits, holes, posts, grooves, linear or nonlinear lines and spaces, and combinations of the foregoing.

8. A method of isolating a nucleic acid, the method comprising:
contacting a hi-functional compound with a sample comprising a nucleic acid at a first pH; and
exposing the hi-functional compound with the nucleic acid bound thereto at a second pH that is higher than the first pH to release the nucleic acid from the bi-functional compound, the bi-functional compound being positively charged at a first pH and negatively charged at a second pH, and represented by Formula I below:

Q-X-Q₁          (Formula I)

wherein Q or Q₁ is

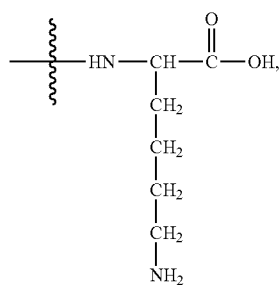

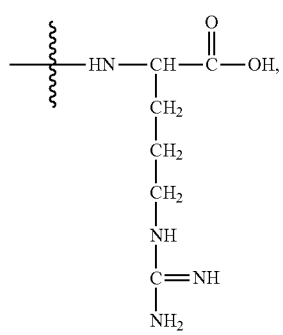

or a combination comprising at least one of the foregoing

X is a compound represented by

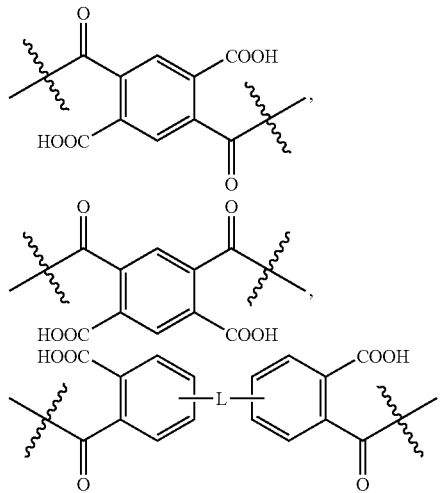

wherein L is a bond, —O—, —CO—, —S—, —SO₂—, —CH₂—, —C(CH₃)₂—, —C(CF₃)₂—, or a combination comprising at least one of the foregoing,

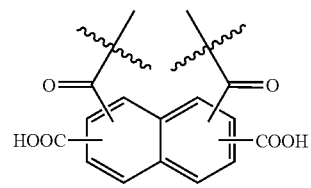

wherein the carbonyl group and the carboxyl group are substituted at any available carbon position except for a ring connection portion,

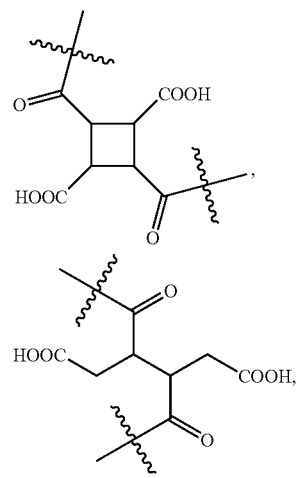

or a combination comprising at least one of the foregoing, or
wherein the bi-functional compound that is positively charged at a first pH and negatively charted at a second pH is linked to at least one monomer comprising monomers represented by Formulas M0, M1, M2, M3, or a combination comprising at least one of the foregoing, below, and wherein the bi-functional compound comprises at least one of a monomer with A and at least one of a monomer with B,

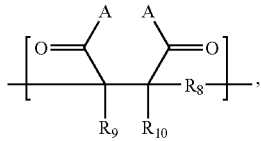
(Formula M0)

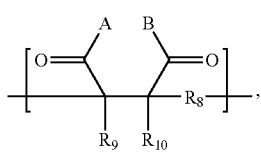
(Formula M1)

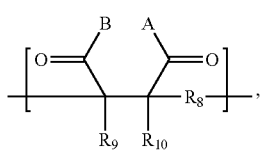
(Formula M2)

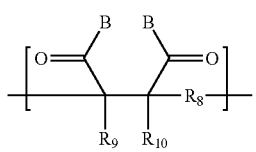
(Formula M3)

wherein A is a group represented by —OH or —$X_2$_$R_{11}$-$Y_2$ where $X_2$ is —O—, —S—, —$NR_{12}$-, or a combination comprising at least one of the foregoing, where $R_{12}$ is hydrogen, halogen, a substituted or unsubstituted $C_1$-$C_{10}$ alkyl, or a combination comprising at least one of the foregoing, $R_{11}$ is a substituted or unsubstituted $C_1$-$C_{10}$ alkylene, a substituted or unsubstituted $C_3$-$C_{10}$ cycloalkylene, a substituted or unsubstituted $C_2$-$C_{10}$ alkenylene, a substituted or unsubstituted $C_2$-$C_{10}$ alkynylene, or a combination comprising at least one of the foregoing, and $Y_2$ is —COOH, —$SO_3H$, —$SO_2H$, —SOH, —$H_2PO_4$, —$HPO_4^-$, —$PO_4^{2-}$, or a combination comprising at least one of the foregoing, and B is

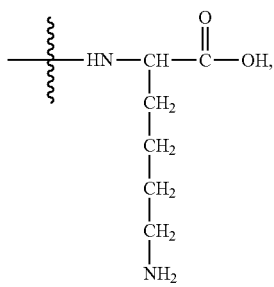

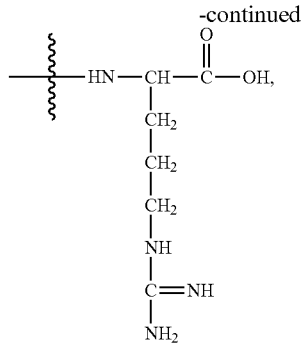

or a combination comprising at least one of the foregoing, and wherein the bi-functional compound comprising A and B has a polymerization degree of about 2 to about 30,000.

9. The method of claim 8, wherein the first pH is about 2 to about 5, and the second pH is about 7 to about 12.

10. The method of claim 8, wherein the bi-functional compound is immobilized on substrate to form a solid support.

11. The method of claim 10, wherein the substrate of the solid support is in the form of a planar plate, multilayered structure, a non-planar structure including a sphere, bead, sieve pillar, or a combination comprising at least one of the foregoing, or a surface of a microchannel in a microfluidic device.

12. The method of claim 10, wherein the substrate of the solid support on which the bi-functional compound is immobilized is glass, magnetic beads, silica, fused silica, polyethylene, polypropylene, slide glass, and silicon wafer, $SiO_2$, $TiO_2$, $Al_2O_3$, $SiN_x$, $TiN_x$, sapphire, metals such as steel, aluminum, titanium, tantalum, silver, gold, platinum, $SiO_2$ or silicon substrates coated with one of these metals, oxides, or nitrides, or a combination comprising at least one of the foregoing.

13. The method of claim 8, wherein the first pH is about 3 to about 4.5, and the second pH about 7 to about 11.

14. The method of claim 8, wherein the first pH is about 3.5 to about 4.5, and the second pH is about 8 to about 11.

15. A solid support on which a bi-functional compound is immobilized, comprising the sequential reaction product of:
a substrate,
a surface treatment agent,
a dianhydride, polyanhydride, and
a nitrogen-containing compound,
wherein the bi-functional compound is positively charged at a first pH and
negatively charged at a second p1-1, and is represented by Formula I below:

Q-X-$Q_1$ (Formula I)

wherein Q or $Q_1$ is

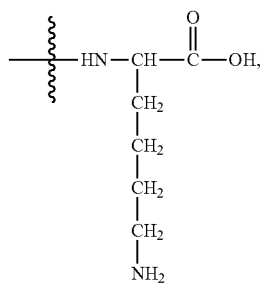

-continued

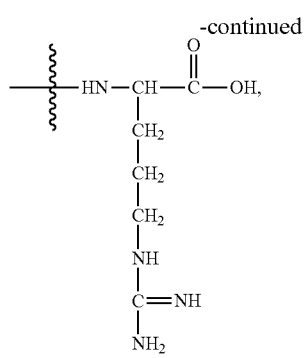

or a combination comprising at least one of the foregoing, and

X is a compound represented by

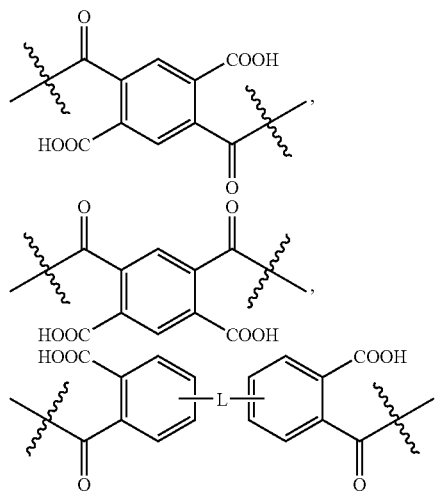

wherein L is a bond, —O—, —CO—, —S—, —SO$_2$—, —CH$_2$—, —C(CH$_3$)$_2$—, C(CF$_3$)$_2$—, or a combination comprising at least one of the foregoing,

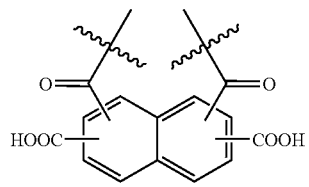

wherein the carbonyl group and the carboxyl group are substituted at any available carbon position except for a ring connection portion,

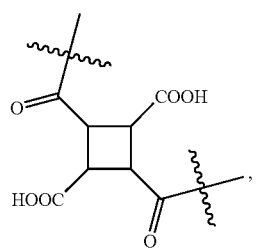

-continued

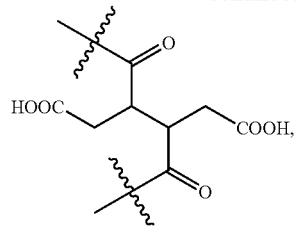

or a combination comprising at least one of the foregoing, or wherein the bi-functional compound is linked to at least one monomer comprising monomers represented by Formulas M0, M1, M2, M3, or a combination comprising at least one of the foregoing, below, wherein the bi-functional compound comprises at least one of a monomer with A and at least one of a monomer with B,

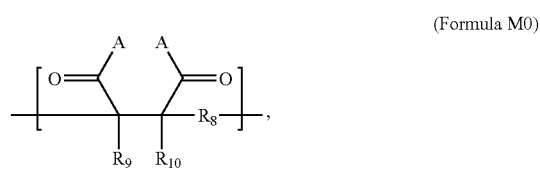
(Formula M0)

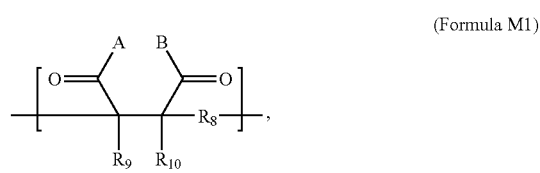
(Formula M1)

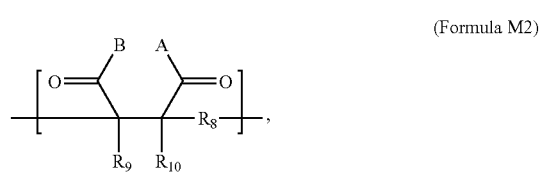
(Formula M2)

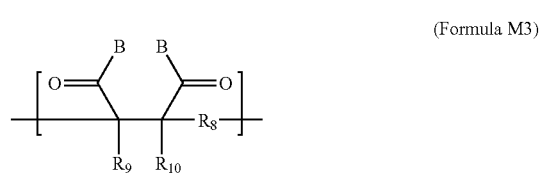
(Formula M3)

wherein A is a group represented by —OH or —X$_2$-R$_{11}$-Y$_2$ where X$_2$ is O—, —S—, —NR$_{12}$— or a combination comprising at least one of the foregoing, where R$_{12}$ is hydrogen, halogen, a substituted or unsubstituted C$_1$-C$_{10}$ alkyl, or a combination comprising at least one of the foregoing, R$_{11}$ is a substituted or unsubstituted C$_1$-C$_{10}$ alkylene, a substituted or unsubstituted C$_3$-C$_{10}$ cycloalkylene, a substituted or unsubstituted C$_2$-C$_{10}$ alkenylene, a substituted or unsubstituted C$_2$-C$_{10}$ alkynylene, or a combination comprising at least one of the foregoing, and Y$_2$ is —COOH, —SO$_3$H, —SO$_2$H, —SOH, —H$_2$PO$_4$, —HPO$_4^-$, —PO$_4^{2-}$, or a combination comprising at least one of the foregoing, and B is
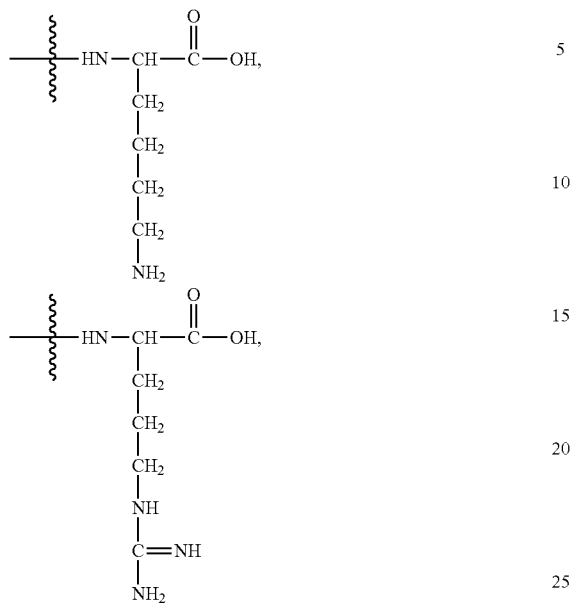
or a combination comprising at least one of the foregoing,
wherein the bi-functional compound comprising A and B has a polymerization degree of about 2 to about 30,000.
* * * * *